United States Patent [19]

Wright et al.

[11] Patent Number: 5,217,992

[45] Date of Patent: Jun. 8, 1993

[54] TOCOTRIENOLS IN THE TREATMENT OF HYPERCHOLESTEROLEMIA, HYPERLIPIDEMIA AND THROMBOEMBOLIC DISORDERS

[75] Inventors: John J. Wright, North Guilford; Bradley C. Pearce, East Hampton; Rex Parker, Branford, all of Conn.; Asaf A. Qureshi, Madison, Wis.

[73] Assignee: Bristol-Myers Squibb Company, New York, N.Y.

[21] Appl. No.: 583,907

[22] Filed: Sep. 17, 1990

Related U.S. Application Data

[63] Continuation-in-part of Ser. No. 416,910, Oct. 4, 1989, abandoned.

[51] Int. Cl.$^5$ .................................. A61K 31/355
[52] U.S. Cl. ............................ 514/458; 514/824
[58] Field of Search ............... 514/458, 824; 549/413

[56] References Cited

U.S. PATENT DOCUMENTS 4,603,142 7/1986 Burger et al. .................. 514/458
4,617,406 10/1986 Willging ......................... 549/413

FOREIGN PATENT DOCUMENTS 2218989A 11/1989 United Kingdom .

OTHER PUBLICATIONS

Tan, Barrie; JAOCS vol. 66(6) Jun. 1989 pp. 770–776.
Qureshi, et al. *Atherosclerosis*, 51: 75–87, (1984).
Qureshi, et al., *J. Biol. Chem.*, 261: 10544–10550, (1986).
Whittle, et al., *Biochem. J.*, 100: 138–145, (1966).
Pennock, et al., *Biochem. and Biophys. Res. Comm.*, 17: 542–548, (1964).
Scott, et al., *Helv. Chim. Acta*, 59: 290–306 (1976).
Urano, et al., *Chem. Pharm. Bull.*, 31: 4341–4345 (1983).
Komiyama, et al., *Chem. Pharm. Bull.*, 37: 1369–1371 (1989).
Hirahara, *Nutrition Reports International*, 36: 161–167 (1987).
Kato, et al., *Yukagaku*, 30: 590–591 (1981).

*Primary Examiner*—Frederick E. Waddell
*Assistant Examiner*—Raymond J. Henley, III
*Attorney, Agent, or Firm*—Michelle A. Kaye

[57] ABSTRACT

This invention relates to the use of tocotrienol, gamma-tocotrienol and delta-tocotrienol in reducing hypercholesterolemia, hyperlipidemia and thromboembolic disorders in mammals. [The isolation of these tocotrienols from natural sources and their chemical synthesis is disclosed.] The chemical synthesis of these tocotrienols is disclosed. The present invention also relates to prodrugs and pharmaceutical compositions of gamma-tocotrienol, delta-tocotrienol and tocotrienol and uses thereof.

6 Claims, 3 Drawing Sheets

(a) $C_6H_6$, Δ ; (b) $AlH_3$, $Et_2O$, −5 C ; (c) NCS, $Me_2S$, $CH_2Cl_2$, −5 C;
(d) THF/HMPA, −78 C ; (e) $PdCl_2$:dppb, $LiEt_3BH$, THF, −20 C ;
(f) $C_2H_4S_2BCl$, $CH_2Cl_2$, −20 C.

(a) Ethyl 2-(Triphenylphosphoranylidene)propionate, $CH_2Cl_2$, 23 C;
(b) PPTS, EtOH, Δ ;(c) $R_1,R_2$-Hydroquinone, $BF_3$, Dioxane, Δ ;(d) pTSA, $C_6H_6$, Δ ;
(e) MemCl, NaH, THF ;(f)$AlH_3$, $Et_2O$, −5 C ;(g) NCS, $Me_2S$, $CH_2Cl_2$, −5 C;
(h) Geranyl-p-Tolysulfane, nBuLi, THF/HMPA, −78 C ;(i) $PdCl_2$·dppb, $LiEt_3BH$, THF, −20 C ;(j)$C_2H_4S_2BCl$, $CH_2Cl_2$, −20 C.

TOCOTRIENOLS IN THE TREATMENT OF HYPERCHOLESTEROLEMIA, HYPERLIPIDEMIA AND THROMBOEMBOLIC DISORDERS

This application is a continuation-in-part of U.S. application Ser. No. 416,910 filed Oct. 4, 1989, Now abandoned.

FIELD OF THE INVENTION

The present invention relates to a method of use employing purified tocotrienol, gamma-tocotrienol, and delta-tocotrienol to treat hypercholesteremia, hyperlipidemia and thromboembolic disorders. The present invention also provides prodrugs of the tocotrienols and method of prepration. Also provided are pharmaceutical compositions and method of use employing those compositions.

BACKGROUND ART

It is generally recognized that high blood cholesterol levels are significant risk factors in cardiovascular disease. Studies have demonstrated that with very few exceptions, populations which consume large quantities of saturated fat and cholesterol have relatively high concentrations of serum cholesterol and a high mortality rate from coronary heart disease. On the other hand, populations which consume large amounts of cereal grains tend to have lower incidences of cardiovascular disease.

Palm oil is commonly classified as a saturated fat and is grouped together with lard, butter fat, hydrogenated vegetable oils, coconut oil and palm kernel oil. Animal and human experiments with palm oil-enriched diets, however, have unexpectedly demonstrated that palm oil feeding does not raise serum cholesterol but in fact it lowers it. An explanation for palm oil's hypocholesterolemic effects despite its fatty acid composition of approximately 50% of the saturated fatty acids and 50% of unsaturated fatty acids was needed.

Studies of cereal grains revealed that barley was particularly effective in lowering lipid levels in animal models. Qureshi et al., *Atherosclerosis*, 51: 75–87, (1984). The ability of barley extracts to lower lipids in vivo prompted the purification and identification of the chemical constituents responsible for cholesterol suppressive activity. alpha-Tocotrienol was recovered from barley extracts using state-of-the-art methods and was designated as the biologically active component based on subsequent in vitro and in vivo evaluation. Qureshi et al., *J. Biol. Chem.*, 261: 10544–10550, (1986). A U.S. patent was issued to The Wisconsin Alumni Research Foundation specifically claiming the use of alpha-tocotrienol for the lowering of lipids, U.S. Pat. No. 4,603,142, to Qureshi et al. (1986).

With the disclosure of alpha-tocotrienol as the hypolipidemic component of barley, we initiated a chemistry program to study this and related compounds. It was found that an important group of minor constituent of palm oil is its tocotrienols.

Purified tocotrienols are best obtained from palm oil or latex using published procedures. Whittle et al., *Biochem. J.*, 100: 138–145, (1966); Pennock et al., *Biochem. and Biophys. Res. Comm.*, 17: 542–548, (1964). Synthesis of alpha-tocotrienol was performed according to the literature method of Urano, et al., *Chem. Pharm. Bull.*, 31: 4341–4345, (1983). However, this method was not acceptable since it provided a mixture of side chain olefin isomers. Other literature methods for the synthesis of alpha-tocotrienol are very lengthy and were not practical Mayer, et al., *Helv. Chim. Acta.* 46: 2517–2526, (1963); Scott, et al., *Helv. Chim. Acta*, 59: 290–306 (1976).

SUMMARY OF THE INVENTION

The present investigation discloses the use of tocotrienol, gamma-tocotrienol and delta-tocotrienol in lowering blood cholesterol, apolipoprotein B, thromboxane $B_2$, platelet factor IV, platelet aggregation, triglycerides and glucose in avian and mammalian systems.

The tocotrienol, gamma-tocotrienol and delta-tocotrienol of the present invention have the following structures:

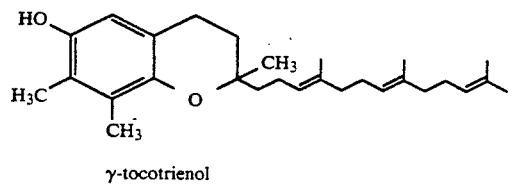

γ-tocotrienol

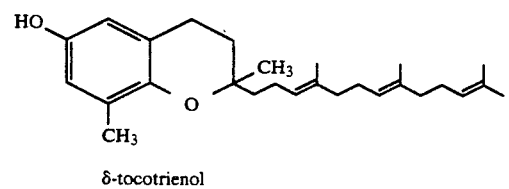

δ-tocotrienol

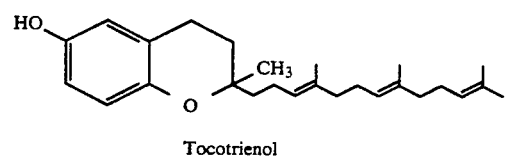

Tocotrienol

These and other homologs of tocotrienols have been chemically synthesized. Experimental details are provided on a new tocotrienol synthesis which provides stereochemically pure materials.

In the method of the present invention, the tocotrienols are administered in a safe and effective amount to lower the blood total and low density lipoprotein cholesterol levels.

These and other advantages and objects of the invention will be apparent to those skilled in the art.

DESCRIPTION OF THE PREFERRED EMBODIMENT

The preferred tocotrienols in the present invention are tocotrienol, gamma-tocotrienol, and delta-tocotrienol, which tocotrienols have the following structures:

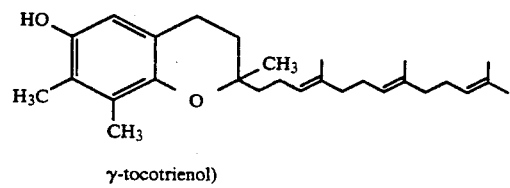

γ-tocotrienol)

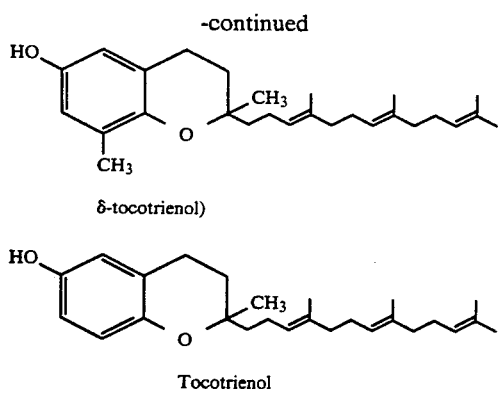

δ-tocotrienol)

Tocotrienol

The tocotrienols as used herein encompasses both the isomers and the racemic mixture. The preferred tocotrienols of the present invention are the natural d-isomer and the d,l-racemic mixture.

The richest sources of tocotrienols are cereals (such as barley, oats, rice, wheat and rye) and vegetable oils such as palm oil and rice bran oil which contain (540 ppm and 570 ppm of gamma-tocotrienol and delta-tocotrienol, respectively). gamma-Tocotrienol or delta-tocotrienol isolated from natural sources are the preferred active components for use in the compositions and method. A natural source of tocotrienol has been described in the literature (Sodano, et al. *Tetrahedron,* 41: 1093-1100 (1985)) and this is the preferred active component for use in the compositions and method. gamma-Tocotrienol has been chemically synthesized and its biological activity is identical to the one isolated from natural sources. delta Tocotrienol was isolated from natural sources but was not chemically synthesized by us. A reasonable method of synthesis for delta-tocotrienol is described on p. 11. ±-delta-tocotrienol has been synthesized by Kato, 4. et al., *Chemistry Letters,* pp. 335-338, (1975).

The tocotrienols of the present invention may be readily administered, to treat hypercholesteremia, hyperlipidemia and thromboembolic disorders, via the alimentary canal in the form of oral doses or by injection in sterile parenteral preparations.

Dosage forms of the compounds can be prepared by combining a compound of the present invention and a non-toxic pharmaceutically acceptable carriers. These carriers can be solid or liquid such as cornstarch, lactose, sucrose. If a solid carrier is used, the dosage forms may be tablets, capsules, powders, troches or lozenges. If the liquid form is used, soft gelatin capsules, syrup or liquid suspensions, emulsions, or solutions in convenient dosage forms will be used.

The dosage ranges will commonly range from about 1-1000 mg/day, but actual amounts are dependent upon, among other factors, patient condition, size and the result to be achieved, as well as other factors known to those skilled in the art of the therapeutic use of such medicinal agents.

A futher objective of the present invention is to provide prodrug esters of the compounds of the present invention, preferably esters of nicotinic acid, succinic acid, or acetic acid.

A further objective of the present invention is to provide a method of preparing a prodrug of the compounds of the present invention which comprises phenol esterification by means of an activated ester such as an anhydride or acid chloride.

The term prodrug, as used herein and in the claims (unless the context indicates otherwise) denotes an analog of an active drug which after administration is capable of undergoing hydrolysis of the ester moiety or oxidative cleavage of the ester moiety so as to release active free drug. The physiologically hydrolyzable esters serve as prodrugs by being hydrolyzed in the body to yield the parent drug per se.

The method and manner of accomplishing these and other objectives of the invention will become apparent from the detailed description which will follow hereinafter.

DETAILED DESCRIPTION OF THE INVENTION

The present application shows that the tocotrienol, gamma-tocotrienol, and delta-tocotrienol components in palm oil act as potent inhibitors of hepatic cholesterol biosynthesis with the concomitant effect of lowering serum total cholesterol and LDL-cholesterol levels in birds and mammals, including humans.

We found that the gamma-tocotrienol and delta-tocotrienol isolated from palm oil contain nearly all of the biological activity and that the alpha-tocotrienol possesses minimal biological activity towards suppression of HMG-CoA reductase.

The results described here are noteworthy in many respects. The variety and magnitude of the biochemical effects of gamma-tocotrienol and delta-tocotrienol especially the suppression of cholesterol biosynthesis is due to their effect at the cellular level, thus producing strong suppression of HMG-CoA reductase, the rate-limiting enzyme for cholesterol biosynthesis in the liver. The liver is the primary site of cholesterol production in humans, swine, quail and chickens.

The remarkable feature of the lowering of the serum cholesterol concentration mediated by feeding substantially pure gamma-tocotrienol or delta-tocotrienol is that only the LDL-cholesterol levels or apolipoprotein B fraction is lowered to a significant extent, particularly in subjects who have a defective LDL-catabolism. This lowering in turn causes a significant lowering of serum total cholesterol.

The temporal action of tocotrienols on cholesterogenesis suggests that first it is directed towards the inhibition of HMG-CoA reductase with a concomitant lowering of cholesterol 7-alpha-hydroxylase activity. The present invention establishes the use of tocotrienol, gamma-tocotrienol or delta-tocotrienol as effective hypocholesterolemic and hypolipidemic agents. The most important additional usage of these compounds are found to be as an antithrombotic agent, significantly decreasing platelet aggregation which could be important in controlling the development of atherosclerosis.

The gamma-tocotrienol and delta-tocotrienol are present in natural foods (barley and rice) in small amounts and are generally regarded as safe for human subjects. The biological activity in tocotrienols is associated with the unsaturated side chain (three double bonds) of three isoprenoid units attached to the chroman ring. Their counterparts, the tocopherols (vitamin E), have saturated isoprenoid side-chains and do not have any significant effect on lipid metabolism in animals. Moreover, the tocopherols are generally chloroplast components, whereas, the tocotrienols are components of cereal seeds. The biological activities of the tocotrienols is in the order of gamma-tocotrienol≃delta-tocotrienol≃tocotrienol>alpha-tocotrienol.

gamma-Tocotrienol has been chemically synthesized and the biological activities of the synthetic gamma-tocotrienol and that purified from natural sources are identical.

Chemical Synthesis of Tocotrienols

Figure 2:
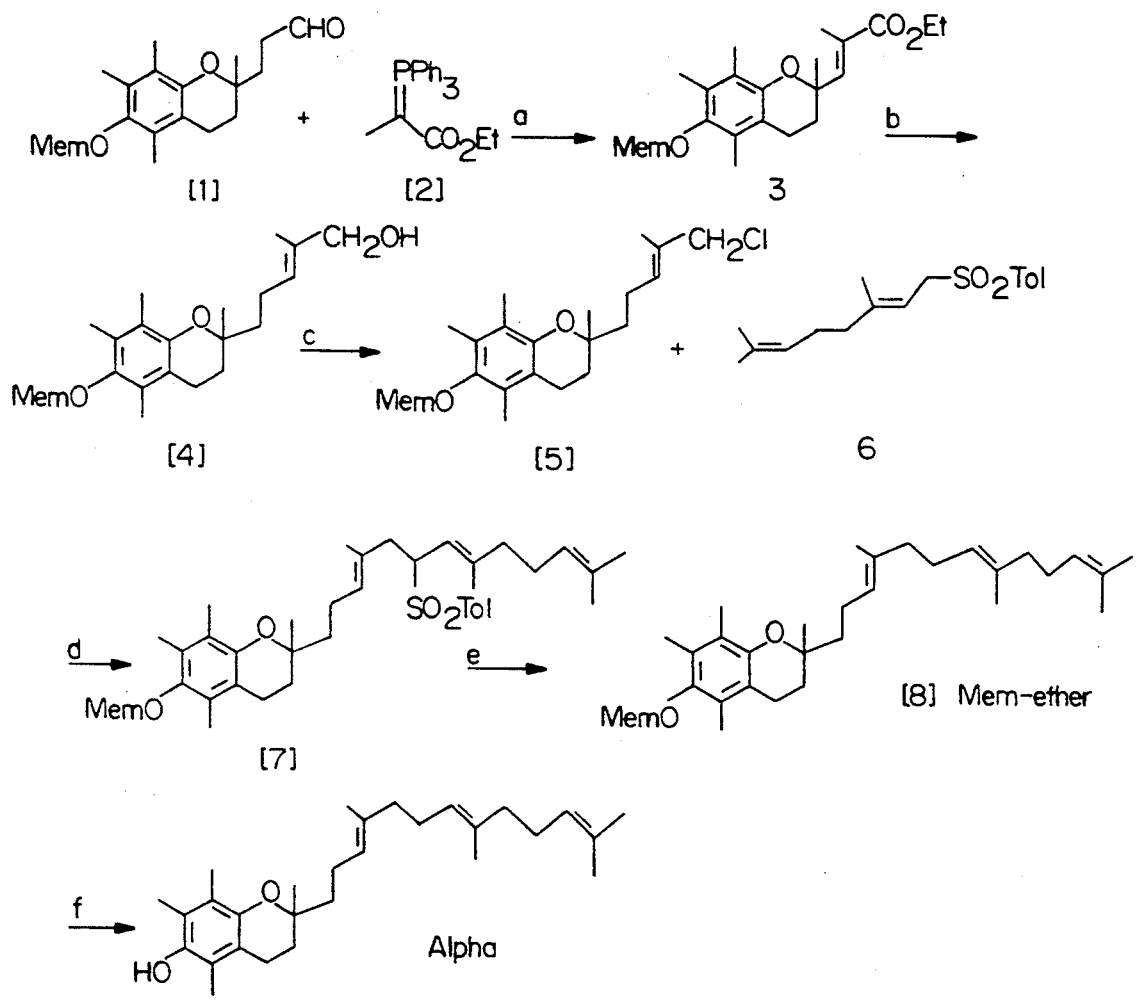
FIG. 2 is an outline the synthesis of alpha-tocotrienol.

The synthesis of alpha-tocotrienol is outlined in FIG. 2. Aldehyde [1] was prepared from the mixture of phenols previously described (Kato et al., *Bull. Chem. Soc. Jpn.*, 41: 1224–1228, (1968)), following protection with 2-methoxy-ethoxy-methyl chloride, ozonolysis and reductive workup. The addition of ethyl 2-(triphenylphosphoranylidene)propionate [2] (Kishi et al., *Tetrahedron*, 37: 3873–3888, (1981)) to aldehyde [1] afforded a 10:1 mixture of E:Z enoates which could be separated by chromatography. The aluminum hydride reduction (Dilling et al., *J. Org. Chem.*, 35: 2971–2976, (1970)) of ester [3] to the allylic alcohol [4] and its conversion to allylic chloride [5] proceeded smoothly (Corey et al., *Tet. Lett.*, 42: 4339–4342, (1972)). The coupling of chloride [5] with sulfone [6] (Grieco et al., *J. Org. Chem.*, 39: 2135–2136, (1974)) provided tocotrienol derivative [7]. Reductive cleavage of [7] occurs with retention of olefin integrity to give [8], using super-hydride catalyzed by palladium(0). Inomatu et al., *Chem. Letters*, pp.1177–1180, (1986). Deprotection of the MEM-ether occurs cleanly using 2-chloro-1,3,2-dithioborolan (Williams et al., *Tet. Lett.*, p.3965, (1983)) to provide all trans alpha-tocotrienol of >95% purity (HPLC).

Figure 3:
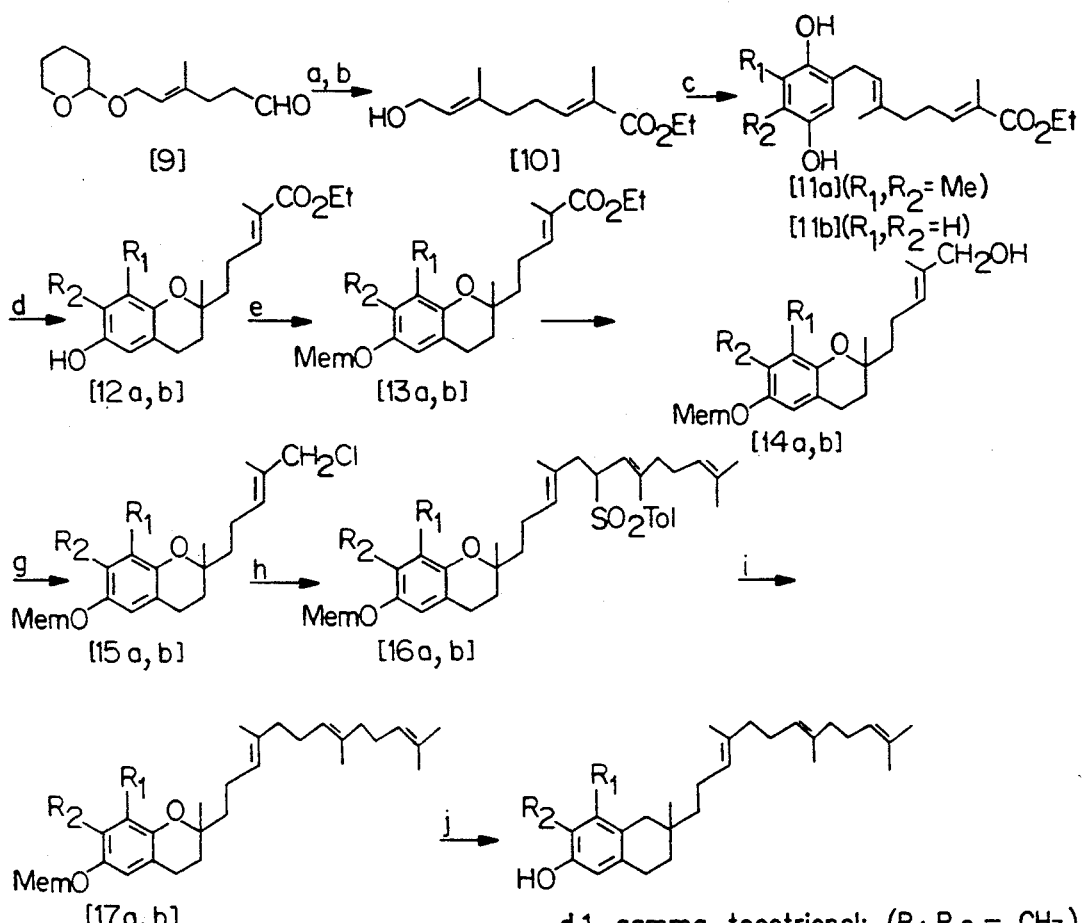
FIG. 3 is an outline of the synthesis of gamma-tocotrienol, and tocotrienol.

The synthesis of gamma-tocotrienol is outlined in FIG. 3. Synthesis of gamma-tocotrienol begins with the known aldehyde [9] (Corey et al. *J. Am. Chem. Soc.*, 92: 6636–6637, (1970)) which is reacted with ethyl 2-(triphenylphosphoranylidene)propionate to provide the all trans ester contaminated by less than 3% of the cis ester ($^1$H-NMR). After removal of the tetrahydropyranyloxy protecting group, the allylic alcohol [10] was condensed with 2,3-dimethyl-hydroquinone to give the oxidatively unstable alkylated hydroquinone [11a]. The hydroquinone was immediately cyclized under the influence of catalytic p-toluenesulfonic acid to yield the benzopyranol [12a], which was directly protected as its methoxyethoxy methyl ether. The oxidatively stable ether [13a] was purified by chromatography on silica gel. Completion of the synthesis of gamma-tocotrienol from ester [13a] proceeds as described for alpha-tocotrienol from the analogous ester [3].

Synthesis of delta-tocotrienol could be readily adapted from FIG. 3 starting with 2-methyl-1,4-hydroquinone 4-monobenzoate (Stern et al., *J. Am. Chem. Soc.*, 69: 869, (1947)), electrophilic aromatic substitution in the monobenzoate being directed into the 6-position.

The fully ring demethylated tocotrienol was prepared in the same manner as gamma-tocotrienol shown in FIG. 3.

EXPERIMENTAL

The following examples are intended for illustrative purpose only and are not to be construed as limiting the invention in sphere or scope.

All temperatures are understood to be in degrees in C. when not specified. Nuclear magnetic resonance (NMR) spectral characteristics refer to chemical shifts (δ) expressed in parts per million (ppm) with tetramethylsilane (TMS) as an internal standard. The relative area reported for the various shifts in the proton NMR spectral data corresponds to the number of hydrogen atoms of a particular functional type in the molecule. The nature of the shifts as to multiplicity is reported as broad singlets (br s), singlets (s), multiplet (m), doublet (d), doublet of doublets (d of d), triplet (t), or quartet (q).

EXAMPLE 1

In Vitro Evaluation of the Biological Activity of Tocotrienols

Rat Hepatocyte Cholesterol Biosynthesis Model

Primary rat parenchymal hepatocytes were prepared from male Wistar rats (180–200 g) at mid-dark in the diurnal cycle by standard collagenase perfusion method as described previously. Ingebritsen et al. *J. Biol. Chem.*, 254:9986–9989, (1979). Aliquots of cells were suspended (100 mg in 2 ml) in Eagle's minimum essential medium (MEM) supplemented with 2% bovine albumin, and preincubated in a shaking water bath at about 37° under 95% $O_2$/5% $CO_2$ with compounds added as given in the data. Tween-80 was employed to aid solubilization of the tocotrienols at 0.2% final conc. as suggested by Qureshi et al. *J. Biol. Chem.*, 261:10544–10550, (1986); in separate studies dimethylsulfoxide vehicle (0.5% v/v) gave results similar to the Tween vehicle data. Following a preincubation of about 15 to about 45 minutes as indicated, cholesterol synthesis in intact cells was assayed by 2-14C-acetate (1.8 mCi/mmol, 0.5 μCi/ml) incorporation for about 30 to about 60 minutes (previously shown to be time-linear) into total digitonin-precipitable sterols. The isolation of this total sterol fraction followed standard methods as described previously (Kates, et al., North Holland-Amsterdam/-Elsevier-New York, *Techniques of Lipidology*, pp.349, 360–364, (1972); and Ingebritsen et al., *J. Biol. Chem.*, 254:9986–9989, (1979). Briefly, samples were precipitated and washed with perchloric acid, saponified in 90% methanol/0.30N NaOH, then quantitatively extracted in hexanes to obtain the non-saponifiable lipids. From this fraction the digitonin-precipitable sterols were obtained. Greater than 98% of the 14C content in this fraction was shown by HPLC to co-elute with authentic cholesterol standard. Percent inhibition was calculated from the average of duplicates vs. triplicate vehicle controls conducted simultaneously.

EXAMPLE 2

Rat Primary Hepatocyte Model

A recent report suggested that alpha-tocotrienol from natural products was an effective inhibitor of cholesterol biosynthesis rat and chicken liver (Qureshi et al., *J. Biol. Chem.*, 261: 10544–10550, (1986)). We therefore synthesized d,l-alpha-tocotrienol, and examined this compound in comparison to a mixture of tocotrienols derived from a natural source; Primary rat hepatocytes were preincubated for about 15 minutes in the presence of 0.2% Tween-80 vehicle and the additions indicated, followed by the assay of cholesterol synthesis by a 60 minutes incorporation of 14C-acetate into total digitoninprecipitable sterols. As shown in Table 1, synthetic alpha-tocotrienol proved to be only weakly active in this system. In contrast, using this assay we unexpectedly detected greater activity in mixtures of gamma-tocotrienol and delta-tocotrienol (tocotrienol-rich fraction (TRF) from palm oil) than could be accounted for by alpha-tocotrienol.

TABLE 1

Synthetic α-Tocotrienol Is Less Effective than a Mixture of Tocotrienols as an Inhibitor of Cholesterol Biosynthesis in Rat Hepatocytes.

| Compound | Conc. μg/ml | % Inhibition | IC$_{50}$ μ/ml |
|---|---|---|---|
| d-α-tocopherol | 210[a] | 0 | — |
| d,1-α-tocotrienol | 41[a] | 4 | |
|  | 210 | 17 | |
| Tocotrienol Mixture | 138 | 31 | 600 |
| (natural source) | 275 | 38 | |
|  | 550 | 45 | |
|  | 1100 | 60 | |
|  | 2200 | 70 | |

[a]For α-tocopherol and α-tocotrienol, 41 μg/ml equals approximately 100 μM, and 210 μg/ml is approximately 500 μM.

Data is given as percent inhibition cholesterol synthesis vs. controls receiving vehicle.

EXAMPLE 3

In order to examine whether the cholesterol synthesis inhibitory activity present in tocotrienol mixtures derived from natural sources (TRF) actually resided in compounds other than alpha-tocotrienol, we chromatographically separated the alpha-tocotrienol, gamma-tocotrienol, and delta-tocotrienol plus alpha-tocopherol from a natural source and examined these compounds in the rat and chicken hepatocytes cholesterol synthesis assay. The primary rat hepatocyte assay for cholesterol bio-synthesis inhibition was conducted as described in Example 2 except the preincubation was about 45 minutes and the 14C-acetate incorporation was about 30 minutes. The indicated compounds were purified from the same natural product source as the mixture used in Example 2. Data from two separate experiments are given in Table 2A. As presented in Table 2A, the results indicate that natural gamma-tocotrienol and delta-tocotrienol are approximately equipotent and are each at least 5 times more active than alpha-tocotrienol in the rat and chicken hepatocyte system. Binary combinations of the components were also examined to test for possible additivity which might reveal activity in alpha tocotrienol. Two-component mixtures of the constituents separated from the tocotrienol mixture were tested under the conditions indentical to Table 2A. As Table 2B shows, only the mixtures containing gamma-tocotrienol or delta-tocotrienol were significantly active, and alpha-tocotrienol did not increase the apparent activity of any other component. These data suggest that as an inhibitor of cholesterol biosynthesis in rat liver cells, alpha-tocotrienol is much less active than gamma-tocotrienol and delta-tocotrienol.

TABLE 2A

Evaluation of α-, γ-, and δ-Tocotrienols Separated from a Natural Product Source as Inhibitors of Cholesterol Synthesis in Isolated Rat Hepatocytes.

| Compound | Expt. # | % Inhibition at μg/ml conc: 125 | 250 | 500 | IC$_{50}$ μg/ml |
|---|---|---|---|---|---|
| d-α-tocopherol | 1 | — | 0 | 2 | no inhib |
|  | 2 | — | 0 | 0 |  |
| d-α-tocotrienol | 1 | — | 8 | 12 | >>1000 |
|  | 2 | 8 | 20 | 33 | 1300 |
| d-γ-tocotrienol | 1 | — | 48 | 60 | 270 |

TABLE 2A-continued

Evaluation of α-, γ-, and δ-Tocotrienols Separated from a Natural Product Source as Inhibitors of Cholesterol Synthesis in Isolated Rat Hepatocytes.

| Compound | Expt. # | % Inhibition at μg/ml conc: 125 | 250 | 500 | IC$_{50}$ μg/ml |
|---|---|---|---|---|---|
|  | 2 | — | 28 | 34 | 61 | 360 |
| d-δ-tocotrienol | 1 | — | 49 | 62 | 260 |
|  | 2 | 26 | 33 | 63 | 340 |

TABLE 2B

Effects of Binary Mixtures on Cholesterol Synthesis in Rat Hepatocytes.

|  | % Inhibition at 250 μg/ml each: |
|---|---|
| α-tocopherol + α-tocotrienol | 3 |
| + γ-tocotrienol | 42 |
| + δ-tocotrienol | 49 |
| α-tocotrienol + γ-tocotrienol | 49 |
| + δ-tocotrienol | 53 |
| γ-tocotrienol + δ-tocotrienol | 64 |

EXAMPLE 4

HepG2 Cell Culture Model—14C-Acetate Incorporation Assay

HepG2 cells obtained from the American Type Culture Collection were routinely passaged in RPMI-1640 plus 10% fetal bovine serum (FBS) and were subcultured into 35 mm diameter wells for experiments. At approximately 60–70% confluence, the medium was changed to 2.0 ml RPMI-1640 plus 7% lipid-depleted serum (LDS) to induce cholesterogenesis as suggested by Burki et al., *J. Lipid Res.*, 28: 1199–1205, (1987). The LDS medium supplement was prepared according to Cham et al., *J. Lipid Res.*, 17: 176–181, (1976). After about 16 hours in LDS containing media, test compounds were added in dimethylsulfoxide vehicle (0.5% v/v final conc.) for the period of time indicated in the data (generally 4 hours). Cholesterol synthesis was then directly determined by the incorporation of 2-14C-acetate (1.8–3.0 mCi/mmol) into digitonin-precipitable sterols essentially as described for the rat hepatocyte methol above. Greater than 97% of the radiolabelled sterol isolated by this procedure was cholesterol as judged by HPLC. Percent inhibition was calculated from the average of duplicates or triplicates vs. controls receiving vehicle.

EXAMPLE 5

HepG2 Cell Culture Model—HMG-CoA Reductase Suppression Assay

HMG-CoA reductase suppression in HepG2 cells was conducted by growing cells in RPMT-1640 plus 10% FBS on 100 mm plates, and when cells reached approximately 75% confluency, inducing with LDS (as described above) for about 6 hours prior to assays. Compounds were added using dimethylsulfoxide vehicle (0.5% v/v, final) and after about hours of incubation at 37°, cells were harvested by scraping. Cell pellets were rinsed and lysed by sonication in 1.7 ml cold 50 mM imidazole-HCL, pH 7.2, 50 mM NaCl, 10 mM EDTA, 10 mM EGTA, 5 mM DTT, and 40 μM leupeptin). Lysates were centriguged at 150×g and the supernatant was centrifuged at 100,000×g in a Beckman airfuge to isolate the post-nuclear total membrane fraction. The membranes were resuspended in 50 mM imidazole-HCl, pH 7.2, 250 mM NaCl, 5 mM DTT, and 20 µM leupeptin and used for the assay of HMG-CoA reductase activity by the radiochemical procedure as described previously by Parker et al., *J. Biol. Chem.*, 264: 4877-4887, (1989). Values were normalized for protein content by the Lowry method as cited previously (ibid). HMG-CoA reductase percent suppression was calculated as the decrease in specific activity of HMG-CoA reductase for treated cells vs. controls receiving vehicle. Averages of duplicate cell determinations assayed in duplicate were taken.

EXAMPLE 6

HepG2 Cell Culture Model—Comparison of alpha-tocotrienol, gamma-tocotrienol and delta-tocotrienol as Inhibitors of Cholesterol Synthesis and Suppressors of HMG-CoA Reductase.

The human hepatoma HepG2 cell culture model was employed to compare the intrinsic activities of the tocotrienols. HepG2 cells were incubated with the indicated compounds for about 4 hours at 10 µM. Cholestrol synthesis was assayed by 14C-acetate incorporation and HMG-CoA reductase suppression was assayed in the isolated microsomal fraction. Cholesterol synthesis inhibition was assayed by 14C-acetate incorporation after preincubation of HepG2 cells with the compounds for about 2 hours or about 4 hours (Example IV). Additional time course studies (not shown) indicated that about 4 hours preincubations were nearly optimal for both compounds. These data show that the HepG2 cell model is more sensitive to the inhibitory effects of tocotrienols as cholesterol biosynthesis suppressors than are rat hepatocytes. As the data in FIG. 1 indicate, gamma-tocotrienol has an even greater relative potency compared to alpha-tocotrienol in the HepG2 cell model than in rat hepatocytes. The IC50s from these studies are given in Table 3, in which it can be seen that the intrinsic potency of gamma-tocotrienol is over 30-fold greater than that of alpha-tocotrienol.

The mechanism of cholesterol synthesis inhibition by tocotrienols involves down-regulation of the limiting enzyme of sterol synthesis, HMG-CoA reductase. In the HepG2 cell culture model, measurements of suppression of total HMG-CoA reductase activity showed that gamma-tocotrienol and delta-tocotrienol were significantly more active than alpha-tocotrienol in supressing HMG-CoA reductase. These data are provided in Table 4. The suppression of HMG-CoA reductase protein expression by gamma-tocotrienol and delta-tocotrienol in HepG2 cells and in rat liver has been confirmed by immunoassy using the Western blot technique (data not shown).

In summary, using in vitro models which reveal the intrinsic pharmacological activity of the tocotrienols (rat hepatocytes and HepG2 cell culture) we discovered that tocotrienols lacking the 5-methyl substituent present in alpha-tocotrienol possess significantly greater cholesterol synthesis suppressive activity as demonstrated in vitro. Furthermore, the racemic synthetic tocotrienols exhibit comparable biological activity to the natural tocotrienols in the cholesterol supression assays (Table 4).

TABLE 3

| | IC$_{50}$ for Cholesterol Synthesis Inhibition in HepG2 Cells by gamma and alpha-Tocotrienol | | | |
|---|---|---|---|---|
| | 2 hr. Incubation | | 4 hr. Incubation | |
| | IC$_{50}$ µM | Rel. Potency | IC$_{50}$ µM | Rel. Potency |
| γ-Tocotrienol | 5.9 | 1.0 | 2.8 | 1.0 |
| α-Tocotrienol | 380 | 0.02 | 94 | 0.03 |

Figure 1:
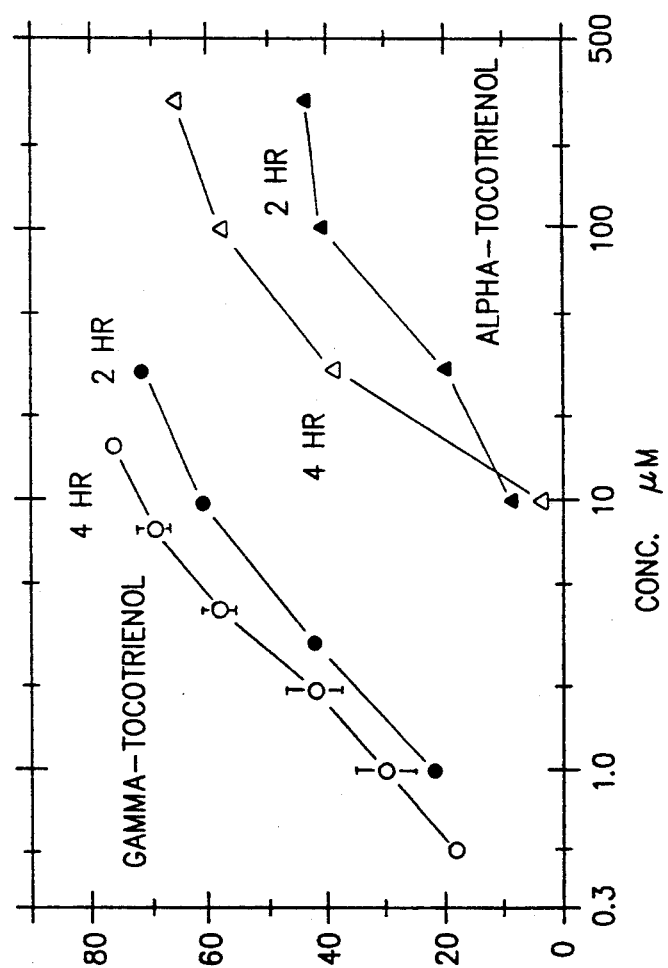
FIG. 1 is a comparison of HepG2 cholesterol synthesis inhibition by tocotrienols.

Data corresponds to FIG. 1

TABLE 4

Tocotrienols Examined in HepG2 Cells: Correlation of Inhibiton of Cholesterol Synthesis from 14C-Ac Incorp. with HMG-CoA Reductase Suppression.

| Compound, 10 µM | % Inhibition 14C-Ac | % Suppression HMG-CoA Reductase |
|---|---|---|
| γ-Tocopherol | 3 | 0 |
| d,1-α-Tocotrienol | 20 | 19 |
| d,1-γ-Tocotrienol | 75 | 65 |
| d,1-Tocotrienol | 69 | 62 |
| d-γ-Tocotrienol | 78 | 64 |
| d-δ-Tocotrienol | 79 | 65 |

EXAMPLE 7

In Vivo Evaluation of d-γ-Tocotrienol and d-δ-Tocotrienol Normocholesterolemic Chickens and Hypercholesterolemic Swine Natural gamma-tocotrienol and delta-tocotrienol were evaluated for their hypocholesterolemic action in normocholesterolemic chickens and genetically hypercholesterolemic swine. Newborn male chicks (10 for each group) were raised on a standard corn-soybean-based control diet for two weeks and then were switched to either control or experimental diets for four weeks. Drug treatment consisted of the addition of gamma-tocotrienol or delta-tocotrienol to the corn-soybean-based diet at a concentration of 20 ppm. At the end of the feeding period, all the birds were fasted (about 36 hours) and refed (about 48 hours) to induce cholesterolgenic emzymes prior to sacrifice. The specific activity of HMG-CoA reductase, total serum cholesterol levels, HDL/LDL cholesterol pools, and serum triglyceride levels were examined (Table 5).

TABLE 5

Effects of gamma-Tocotrienol and delta-Tocotrienols on Lipid Metabolism in 6-Week Old Male Chichens

| | Corn Control Diet (CCD) | CCD+ 20 ppm d-γ-Tocotrienol [% of Control] | CCD+ 20 ppm d-δ-Tocotrienol [% of Control] |
|---|---|---|---|
| HMG-CoA Reductase Specific Activity | 1086.9(±114.0) | 494.2(±22.9)[45.5] | 550.2(±33.8)[50.6] |
| Serum Cholesterol mg/dl | 197.0(±5.2) | 150.5(±4.2)[76.4] | 140.9(±3.1)[71.5] |
| HDL-Cholesterol mg/dl | 107.4(±7.0) | 102.3(±4.5)[95.3] | 98.7(±8.4)[91.9] |
| LDL-Cholesterol mg/dl | 76.0(±5.3) | 43.1(±8.3)[56.7] | 40.8(±6.6)[53.7] |
| HDL/LDL | 1.413 | 1.669 | 2.419 |

TABLE 5-continued

Effects of gamma-Tocotrienol and delta-Tocotrienols on Lipid Metabolism in 6-Week Old Male Chichens

|  | Corn Control Diet (CCD) | CCD+ 20 ppm d-γ-Tocotrienol [% of Control] | CCD+ 20 ppm d-δ-Tocotrienol [% of Control] |
|---|---|---|---|
| Serum Triglycerides mg/dl | 115.2(±13) | 95.4(±5.9)[82.8] | 88.7(±7.3)[77.0] |
| HDL-cholesterol mg/dl | 102.3(±3.0) | 89.0(±2.9)[87.0] | |
| LDL-Cholesterol mg/dl | 52.8(±1.1) | 28.9(±1.2)[54.8] | |
| HDL/LDL | 1.938 | 3.080 | |
| Serum Triglycerides mg/dl | 63.4(±2.1) | 63.9(±1.6)[100.7] | |

Similarly, synthetic gamma-tocotrienol was administered to male chicks at 50 ppm using the same protocol except HMG-CoA reductase levels were not determined. The data for this study is shown in Table 6.

TABLE 6

Effects of d,1-γ-Tocotrienol on Lipid Metabolism in 6-Week Old Male Chickens.

|  | Corn Control Diet (CCD) | CCD + 20 ppm d,1-γ-Tocotrienol [% of Control] |
|---|---|---|
| Serum Cholesterol mg/dl | 158.8(±9.0) | 121.2(±2.2)[76.3] |

The drug treated birds exhibited significant reductions in hepatic HMG-CoA reductase, total serum cholesterol and serum triglyceride levels over control diet fed chickens. In addition, the drug treated birds showed significant enhancements in their HDL/LDL cholesterol as a measure of atherogenic index.

Genetically hypercholesterolemic swine (3 per group) were fed for four weeks on either a standard corn-soybean-based control diet or an experimental diet. The experimental diet consisted of the standard mix containing either gamma-tocotrienol or delta-tocotrienol at 75 ppm. The same protocol used for the chicken study was used for the swine group, except HMG-CoA reductase levels were not determined in this case. Again, the drug treated animals exhibited marked reductions in serum cholesterol and triglyceride levels. The HDL/LDL atherogenic index as before improved dramatically with drug treatment (Table 7).

TABLE 7

Effects of gamma-Tocotrienol and delta-Tocotrienol on Lipid Metabolism in Genetically Hypercholesterolemic Swine

|  | Corn-Soybean Meal Control Diet (CSMCD) | CSMCD + 75 ppm d-γ-Tocotrienol [(% of Control] | CSMCD + 75 ppm d-δ-Tocotrienol [% of Control] |
|---|---|---|---|
| Serum Cholesterol mg/dl | 406.7(±12.8) | 212.8(±9.0)[51.3] | 214.9(±18.6)[47.7] |
| HDL-Cholesterol mg/dl | 28.8(±1.1) | 29.8(±2.9)[104.5] | 34.4(±1.9)[105.3] |
| LDL-Cholesterol mg/dl | 367.1(±15.7) | 172.8(±7.1)[46.0] | 182.2(±8.2)[44.8] |
| HDL/LDL | 0.078 | 0.172 | 0.189 |
| Serum Triglycerides mg/dl | 67.9(±2.8) | 50.9(±3.1)[76.4] | 44.4(±1.3)[70.3] |

EXAMPLE 8

Antithrombotic Properties of Gamma-Tocotrienol

The antithrombotic properties of gamma-tocotrienol were evaluated in a rabbit biolaser ear chamber model. Fasted rabbits were orally dosed with either vehicle or vehicle plus gamma-tocotrienol at 100 mg/kg. An erythrocyte contained within a capillary, near the ear surface, is ruptured with a laser shot, thereby releasing platelet aggregating ADP. gamma-Tocotrienol inhibited platelet aggregation 37% at about 2 hours after oral dosing, 44% after about 4 hours and 25% after about 6 hours as measured by averaging the mean thrombus area over 10 trials.

TABLE 8

Effects of "Palm Vitee" or Corn Oil on the Serum Total Cholesterol Concentration in Hypercholesterolemic Humans[1]

|  | Total Cholesterol Concentration in Serum (mg/100 ml) | | | |
|---|---|---|---|---|
|  | Baseline Value 1st | Feeding Period | | |
| Nutritional State | Two Weeks 0 - Time | 14 days | 28 days | 42 days |
| Placebo (corn oil capsules) | 290 ± 30(100) | 286 ± 27(99) | 296 ± 31(102) | |
| Palm Vitee capsules | 294 ± 34[a](100)[2] | 257 ± 34[a](91) | 249 ± 27[a](85) | |
| Corn Oil capsules/ Palm Vitee capsules[3] | 296 ± 31[a](100)[2] | 252 ± 25[a](89) | 243 ± 20[b](82) | 238 ± 21[b](83) |
| Palm Vitee | 249 ± 27[a](100)[2] | 252 ± 26[a](101) | 244 ± 21[a](98) | 257 ± 24[a](103) |

TABLE 8-continued

Effects of "Palm Vitee" or Corn Oil on the Serum Total Cholesterol Concentration in Hypercholesterolemic Humans[1]

| | Total Cholesterol Concentration in Serum (mg/100 ml) | | | |
|---|---|---|---|---|
| | Baseline Value 1st | | Feeding Period | |
| Nutritional State | Two Weeks 0 - Time | 14 days | 28 days | 42 days |
| Capsules/ Corn Oil Capsules[4] | | | | |

[1]Time of drawing the blood was 0800. The subjects were fasted for 12 hours prior to taking the samples.
[2]Percentages of increases or decreases in respect to baseline value.
[3]Subjects were on corn oil capsules for four weeks and then transferred to Palm Vitee capsules for six weeks.
[4]Subjects were on Palm Vitee for four weeks and then transfereed to corn oil for six weeks.
[a-b]Values not sharing a common superscript are different $p < 0.05$.

When the corn oil placebo group now on "Palm Vitee" capsules for several weeks also showed a drop in serum cholesterol levels and other parameters as shown in Table 8.

Hypercholesterolemic human subjects (serum cholesterol levels 302.5 mg/dl) on pure gamma-tocotrienol capsules (50 mg/capsule) showed a dramatic decrease in their serum cholesterol levels of 35% after 4 weeks of feeding. This indicates that gamma-tocotrienol may be the most potent cholesterol inhibitor in Palm Vitee capsules.

EXAMPLE 9

Comparison of In Vivo Effectiveness of Nicotinate, Acetate, and Free Phenol Forms of d,l-γ-Tocotrienol in the Acute Rat HMGCoA Reductase Suppression Model.

Using an acute rate model for suppression of hepatic HMGCoA reductase, the effectiveness of three forms of d,l-γtocotrienol were compared in vivo. In this assay system, the test agents were administered by intragastric intubation as solutions dissolved in olive oil vehicle. Four hours after administration of test agents, rat liver HMGCoA reductase total activity levels were determined by standard techniques in this laboratory. The assay methodology for determination of total HMGCoA reductase activity, and the demonstration that total reductase activity is proportional to enzyme protein mass, have been previously reported (R. A. Parker, et al., 1989, J. Biol. Chem., 264:, 7877-7887; and in the initial patent application).

TABLE 9

| | Hepatic HMGCoA Reductase Activity | | |
|---|---|---|---|
| Condition[a] | N | mU/mg (mean ± SEM) | % of Control |
| Vehicle Control | 5 | 479 ± 88 | 100 |
| Compound of Ex. 24 | 5 | 266 ± 24 | 56 |
| Compound of Ex. 33 | 4 | 236 ± 23 | 49 |
| Compound of Ex. 34 | 5 | 156 ± 21 | 33 |

[a]All doses were given in olive oil vehicle, and are equivalent to 80 mg/kg Example 23 (195 μmol/kg); viz., 88 mg/kg for Example 32 and 100 mg/kg for Example 33.
[b]$P < 0.05$ vs. control.
[c]$P < 0.01$ vs. control, and $P < 0.05$ vs. Example 23.

EXAMPLE 10

3,4-dihydro-6-[(2-methoxyethoxy)methoxy]-2,5,7,8-tetramethyl-2H-1-benzopyran-2-propanal, [1]

A mixture (about 60:40) of 2,5,7,8-tetramethyl-2-(4-methyl-3-pentenyl)-2H-1-benzopyran-6-ol and its cyclized isomer (42.5 g, 0.148 mole) dissolved in about 50 ml of dry THF was added dropwise to a cooled (5°) oil-free suspension of sodium hydride [6.5 g (60%), 0.162 mole) in about 200 ml of dry THF. 2-Methoxyethoxymethyl chloride (18.52 ml, 0.162 mole) was added dropwise to the mixture, initiating hydrogen release. After hydrogen evolution ceased, the solution was warmed to about 23° and stirred an additional 18 hours. The solution was poured into 1N NaOH and the product was extracted into ether. The organic layers were washed with brine and dried ($K_2CO_3$). Evaporation in vacuo yielded 60 g of a yellow oil.

The above oil was used directly in the ozonolysis step, whereby it was dissolved in about 400 ml of $CH_2Cl_2$ containing 12 ml of MeOH. The solution was cooled to about −78° while ozone was bubbled through the mixture. The reaction was followed by TLC (1:1 $Et_2O$:Hexanes) and when the less polar mixture of ethers was reduced to about ¼, the process was stopped. The mixture warmed to about −5° and dimethyl sulfide (12 ml) was added. After stirring for about 12 hours at about 23°, the volatile components were stripped off in vacuo leaving a yellow oil which was directly purified by flash chromatography (gradient 9:1 to 1:1 Hexanes:$Et_2O$) to give [1], 26.18 g, as a pale yellow oil:

IR (film) 2925, 1725, 1450, 1250, 980 cm$^{-1}$; $^1$H NMR ($CDCl_3$) δ1.26 (s, 3H), 1.7-2.0 (m, 4H), 2.05 (s, 3H), 2.13 (s, 3H), 2.17 (s, 3H), 2.62 (m, 4H), 3.43 (s, 3H), 3.61 (t, 2H), 3.97 (t, 2H), 4.92 (s, 2H), 9.79 (s, 1H); MS m/e 351 (MH+).

Anal. Calcd. for $C_{20}H_{30}O_5$:
C, 68.55; H, 8.63.
Found: C, 68.20; H, 8.80.

EXAMPLE 11

Ethyl 5-[3,4-dihydro-6-[(2-methoxyethoxy)methoxy]-2,5,7,8-tetramethyl-2H-1-benzopyran-2-yl]-2-methyl-2-(E)-pentenoate, [3]

A benzene solution (100 ml) of aldehyde [1] (5.0 g, 14.3 mmole) and ethyl 2-(triphenylphosphoranylidene) propionate (7.76 g, 21.4 mmole) were heated to reflux for about 30 minutes. at which time TLC (2:1 $Et_2O$:Hex.)indicated a trace of aldehyde remaining which did not react with further heating. An additional amount of phosphorane (1.56 g, 4.29 mmole) was added and the mixture was heated for an additional 30 minutes at which time TLC analysis indicated the reaction to be complete. The benzene was stripped in vacuo and the solid material was triturated with hexanes and filtered. Concentration of the hexanes yielded 7.3 g of a yellow oil which was purified by flash chromatography (gradient 12:1 to 4:1 Hexanes: Et$_2$O). A 1.138 g mixture of the less polar Z isomer (23%, PMR) along with the title compound was first off the column followed by 3.10 g, 7.14 mmole, 50% of the pure title compound [3] which was purified for analysis by Kugelrohr distillation (bath 210°/0.1 mm) yielding a colorless oil:

IR (film) 2978, 2931, 2878, 1710, 1459, 1399, 1252, 1098, 981 cm$^{-1}$;

$^1$H NMR (CDCl$_3$)δ1.24 (s, 3H), 1.26 (t, J=6.1 Hz, 3H), 1.58–1.85 (m, 4H), 1.80 (s, 3H), 2.06 (s, 3H), 2.12 (s, 3H), 2.16 (s, 3H), 2.27–2.34 (m, 2H), 2.57 (t, J=5.7 Hz, 2H), 3.38 (s, 3H), 3.59 (m, 2H), 3.93 (m, 2H), 4.15 (q, J=6.1 Hz, 2H), 4.92 (s, 2H), 6.75 (t, J=6.2 Hz, 1H); MS m/e 435 (MH+).

Anal. Calcd. for C$_{25}$H$_{38}$O$_6$:
C, 69.10; H, 8.82
Found: C, 68.89; H, 8.73.

EXAMPLE 12

5-[3,4-Dihydro-6-[(2-methoxyethoxy)methoxy]-2,5,7,8-tetramethyl-2H-1-benzopyran-2-yl]-2-methyl-2(E)-penten-1-ol [4]

To a suspension of LiAlH$_4$ (1.138 g, 30 mmole) in about 70 ml of dry ether cooled to about −5° was added AlCl$_3$ (1.333 g, 10 mmole) portionwise. After stirring the slurry of alane for about 0.5 hours at about −5°, ester [3] (2.854 g, 6.58 mmole) was added as an ether solution (20 ml) dropwise over a period of about 0.5 hours. After about 0.25 hours at about −5°, TLC (1:1 Hex.: Et$_2$O) indicated complete reduction of the ester and the mixture was quenched by the slow addition of saturated Na$_2$SO$_4$ solution. The aluminum salts were filtered and washed well with methanol. The combined organic fractions were washed with water, extracted into fresh ether and dried (Brine, MgSO$_4$). Concentration in vacuo gave a colorless oil (2.386 g, 6.09 mmole, 93%) of [4], an analytical sample was prepared by Kugelrohr distillation (TLC indicated trace decomposition):

IR (film) 3460, 2940, 1465, 1260, 990 cm$^{-1}$;

$^1$H NMR (CDCl$_3$)δ1.24 (s, 3H), 1.25–1.85 (m, 4H), 1.65 (s, 3H), 2.06 (s, 3H), 2.07–2.19 (m, 2H), 2.12 (s, 3H), 2.16 (s, 3H), 2.56 (t, J=5.6 Hz, 2H), 3.38 (s, 3H), 3.59 (m, 2H), 3.94 (m, 4H), 4.92 (s, 2H), 5.40 (t, J=5.02 Hz, 1H); MS m/e 392 (M+).

Anal Calcd. for C$_{23}$H$_{36}$O$_5$:
C, 70.38; H, 9.25,
Found: C, 70.21; H, 9.30.

EXAMPLE 13

3,4-dihydro-6-[(2-methoxyethoxy)methoxy]-2,5,7,8-tetramethyl-2-[6-[(4-methylphenyl)sulfonyl]4,8,12-trimethyltrideca-3-(E),7(E),11-trienyl]-2H-1-benzopyran, [7]

Dimethylsulfide (0.59 ml, 7.98 mmole) was added dropwise to a solution of N-chlorosuccinimide (977 mg, 7.32 mmole) in about 25 ml of dry CH$_2$Cl$_2$ cooled to −5°. The white suspension was stirred for about 0.25 hours while the alcohol [4] (2.609 g, 6.66 mmole) was added as a CH$_2$Cl$_2$ solution 5(ml). The clear solution was stirred for about 1.5 hours at about −5° at which time TLC (2:1 Hex.: Et$_2$O) indicated complete conversion to a less polar spot. The CH$_2$Cl$_2$ was removed in vacuo (<40°) leaving an oily solid. The material was triturated with hexanes, filtered, and concentrated in vacuo (<40°) to a pale yellow oil. The oil was immediately flushed through a pad of silica gel (gradient 8:1 to 4:1 Hex.: Et$_2$O) to give the unstable chloride [5] as a pale yellow oil (2.44 g, 5.95 mmole, 89%). The chloride could be stored for a short period at −20° under nitrogen prior to use in the coupling step.

3,7-dimethyl-1-p-toluenesulfonyl-2-(E)-6-octadiene [(Gosselin et al., Synthesis, pp.876–881, (1984)), (2.086 g, 7.14 mmole)] was dissolved in about 15 ml of a dry THF/HMPA; 4:1 mixture. The solution was cooled to about −78° under nitrogen and butyllithium [2.98 ml(2.5M hexanes), 7.44 mmole] was added dropwise giving a rise to a red-orange anion. After stirring for about 2 hours at about −78°, chloride [5] (2.44 g, 5.95 mmole) was added dropwise as a THF solution (3 ml) to the anion and stirring was continued at about −78° for about 4 hours. The mixture was quenched at about −78° with pH 7.0 buffer solution, poured into water and extracted into ether. The organic layers were dried (brine, MgSO$_4$) and concentrated in vacuo to give a yellow oil which was purified by flash chromatography (gradient 8:1 to 4:1 Hexanes: Et$_2$O) to yield the sulfone [7] (3.722 g, 5.59 mmole, 94%) as pale yellow oil:

IR (film) 2950, 1460, 1150, 980 cm$^{-1}$;

$^1$H NMR (CDCl$_3$)δ1.16 (d, 3H), 1.18 (s, 3H), 1.47, 1.48 (s, 3H) 1.4–1.5 (m, 4H), 1.56 (s, 3H), 1.66 (s, 3H), 1.75 (m, 2H), 1.89 (m, 4H), 2.03 (s, 3H), 2.10 (s, 3H), 2.14 (s, 3H), 2.21 (t, J=9.98 Hz, 1H), 2.41 (s, 3H), 2.53 (t, J=5.68 Hz, 2H), 2.82 (d, J=10.51 Hz, 1H), 3.38 (s, 3H), 3.58 (m, 2H), 3.83 (m, 1H), 3.93 (m, 2H), 4.84 (d, J=8.62 Hz, 1H), 4.91 (s, 2H), 4.99 (m, 1H), 5.13 (t, J=5.77 Hz, 1H), 7.27 (d, J=6.71 Hz, 2H), 7.68 (d, J=6.72 Hz, 2H), MS m/e 666 (M+).

Anal. Calcd. for C$_{40}$H$_{58}$O$_6$S$_1$:
C, 72.04; H, 8.77.
Found: C, 71.86; H, 8.91.

EXAMPLE 14

3,4-dihydro-6-[(2-methoxyethoxy)methoxy]-2,5,7,8-tetramethyl-2-(4,8,12,-trimethyltrideca-3-(E),11-trienyl)-2H-1-benzopyran, [8]

Sulfone [7] (3.644 g, 5.47 mmole) was dissolved in 25 ml of dry THF and cooled to about 0° under nitrogen. Palladium [1,4-bis(diphenylphosphino)butane]-chloride (165 mg, 0.27 mmole) was added to the THF solution. Lithium triethylborohydride [10.9 ml (1.0M THF), 10.9 mmole] was added dropwise to the suspension of PdCl$_2$ dppb over a period of about 10 minutes. The yellow-tan heterogeneous mixture goes to a clear brown homogeneous solution upon addition of all the hydride. The mixture was stirred for about 5 hours at about 0°, then at about −20° for about 12 hours at which time TLC (1:1 Hex.:ET$_2$O) indicated the reaction to be approximately 80% complete. An additional amount of palladium catalyst (41 mg, 0.07 mmole) was added and the mixture was stirred an additional 4 hours at about 0° at which time TLC indicated complete conversion. The reaction mixture was quenched at about 0° with excess potassium cyanide in 1N NaOH, then poured into water and extracted with ether. The organic layers were washed with water, dried (brine, MgSO$_4$) and concentrated in vacuo to give a light brown oil. Purification by flash chromatography (gradient 20:1 to 10:1 Hexanes: Et$_2$O) yield [8] (2.675 g, 5.22 mmole, 96%) as a colorless oil:

IR (film) 2960, 1460, 1063, 985 cm$^{-1}$;

$^1$H NMR (CDCl$_3$)δ1.23 (s, 3H), 1.58 (s, 9H), 1.66 (s, 3H), 1.77 (m, 2H), 1.90–2.2 (m, 12H), 2.07 (s, 3H), 2.12 (s, 3H), 2.16 (s, 3H), 2.56 (t, J=6.77 Hz, 2H), 3.39 (s, 3H), 3.59 (m, 2H), 3.94 (m, 2H), 4.92 (s, 2H), 5.10 (m, 3H), MS m/e 512 (M+).

Anal. Calcd. for $C_{33}H_{53}O_4$:
C, 77.30; H, 10.23.
Found: C, 77.23; H, 10.23.

EXAMPLE 15

3,4-dihydro-2,5,7,8-tetramethyl-2-(4,8,12-trimethyl-tridec-3(E), 7(E),11-trienyl)-2H-1-benzopyran-6-ol [alpha-tocotrienol]

MEM-ether [8] (1.27 g, 2.48 mmole) was dissolved in about 6 ml of dry $CH_2Cl_2$ and cooled to about $-78°$ under $N_2$. 2-Chloro-1,3,2-dithioborolan (0.47 ml, 4.96 mmole) was added to the $CH_2Cl_2$ solution and the mixture was placed into a $-20°$ freezer for about 20 hours. The solution was poured into saturated $NaHCO_3$ solution, extracted with fresh $CH_2Cl_2$, dried ($MgSO_4$) and concentrated in vacuo to give a foul smelling oil. The oil was purified by flash chromatography (20:1 Hexanes:$Et_2O$) to yield alpha-tocotrienol (1.07 g, 2.52 mmole) as a colorless oil which still smelled of sulfur but was one spot by TLC (2:1 Hexanes:$Et_2O$). The product was further purified by crystallization ($\times 3$) from cold ($-78°$) pentane to give an odorless white solid, mp 25°-28°, 716 mg, 1.69 mmole, 68%. HPLC analysis (IB-Sil C18; 91:9 $MeCN:H_2O$) indicated one major band of >94% purity by total integration. alpha-Tocotrienol:

IR (film) 3460, 2940, 1460, 1380, 1260, 1090 cm$^{-1}$;
$^1$H NMR (CDCl$_3$)$\delta$1.09 (s, 3H), 1.43 (s, 3H), 1.44 (s, 6H), 1.52 (s, 3H), 1.63 (m, 2H), 1.78-1.95 (m, 12H), 1.95 (s, 6H), 2.00 (s, 3H), 2.45 (t, J=6.80 Hz, 2H), 4.01 (s, 1H), 4.94 (m, 3H); MS m/e 424 (M+).

Anal. Calcd. for $C_{29}H_{44}O_2$:
C, 82.03; H, 10.45.
Found: C, 82.04; H, 10.87.

EXAMPLE 16

Ethyl 2,6-dimethyl-8-[(tetrahydro-2H-pyran-2-yl)oxy]-2(E),-6(E)-octadienoate

Aldehyde [9] (20.285 g, 0.097 mole) [Corey et al., *J. Am. Chem. Soc.*, 92: 6636-6637, (1970)] and ethyl 2-(triphenylphosphoranylidene)propionate (41.96 g, 0.12 mole) were dissolved, with cooling (0°, 30 minutes) in about 300 ml of dry $CH_2Cl_2$. After about 18 hours at about 23°, TLC (2:1 Hexanes:$Et_2O$) indicated the reaction complete and the solvent was removed in vacuo. The oily yellow solid was triturated with 1:1 hexanes:ether and the solid material was removed by filtration. The solvents were removed in vacuo to give a yellow oil which was purified by flash chromatography (gradient 15:1 to 7:1 Hexanes:$Et_2O$) to give the title compound (26.7 g, 0.09 mole, 93%) as a colorless oil:

IR (film) 2952, 1715, 1272, 1120, 1030 cm$^{-1}$;
$^1$H NMR (CDCl$_3$)$\delta$1.15 (t, J=7.8 Hz, 3H), 1.55 (m, 4H), 1.73 (s, 3H), 1.78 (m, 2H), 1.85 (s, 3H), 2.1-2.4 (m, 4H), 3.52 (m, 1H), 3.90 (M, 1H), 4.07 (m, 2H), 4.19 (q, J=7.8 Hz, 2H), 4.65 (t, J=3 Hz, 1H), 5.4 (t, J=7.5 Hz, 1H), 6.75 (t, J=7 Hz, 1H); MS m/e 297 (MH+).

Anal. Calcd. for $C_{17}H_{28}O_4$:
C, 68.89: H, 9.53.
Found: C, 68.94; H, 9.39.

EXAMPLE 17

Ethyl 2,6-dimethyl-8-hydroxy-2(E), 6(E)-octadienoate, [10]

Ethyl 2,6-dimethyl-8-[tetrahydro-2H-pyran-2yl)oxy]-2 (E),6(E)-octadienoate (10.20 g, 0.034 mole) was dissolved in about 300 ml of absolute ethanol containing pyridinium tosylate (700 mg, 2.79 mmole) and the mixture was heated under reflux for about 2 hours. The solution was poured into water and the ester was extracted into ether. The ether layers were washed with water, dried (brine, $MgSO_4$) and concentrated in vacuo to an oil (7.1 g). The product was purified by flash chromatography (gradient 10:1 to 1:1 Hexanes:Ether) to yield 980 mg of an oil which contained the title compound contaminated by the less polar 2E,6Z isomer, followed by the all trans ester [10] (6.06 g, 0.029 mole, 84%) as a colorless oil which was Kugelrohred for analytical purposes:

IR (film) 3420, 2994, 2944, 1715, 1280, 750 cm$^{-1}$;
$^1$H NMR (CDCl$_3$)$\delta$1.30 (t, J=6.5 Hz, 3H), 2.71 (s, 3H), 2.87 (s, 3H), 2.08-2.20 (m, 4H), 4.19 (m, 4H), 5.44 (t, J=6.5 Hz, 1H), 6.73 (t, J=6.5 Hz, 1H); MS m/e 213 (MH+).

Anal. Calcd. for $C_{12}H_{20}O_3$:
C, 67.90; H, 9.50.
Found: C, 67.85; H, 9.58.

EXAMPLE 18

Ethyl 5-[3,4-dihydro-6-[(2-methoxyethoxy)methoxy]-2,7,8-trimethyl-2H-1-benzopyran-2-yl]-2-methyl-2(E)-pentenoate, [13a]

2,3-Dimethylhydroquinone (4.183 g, 0.03 mole) and ester [10] (3.213 g, 0.015 mole) were dissolved in warm (65°) dry dioxane (50 ml) under nitrogen. Boron trifluoride etherate (0.47 ml, 3.8 mmole) was added and the mixture was stirred under nitrogen for about 3 hours at about 65° at which time TLC (3:2 Hexanes:$Et_2O$) indicated complete reaction. The solvent was removed in vacuo and the residue was dissolved in ether. The ether layers were washed successively with aqueous sodium bicarbonate and sodium hydrosulfite, then dried (brine, $MgSO_4$) and concentrated in vacuo to an oily solid. The residue was triturated with 3:1 (Hexanes:$Et_2O$) to remove unreacted 2,3-dimethylhydroquinone by filtration. Concentration of the organic layers in vacuo yielded 4.93 g of crude [11a] isolated as an amber oil.

The above oil is very oxidatively unstable and was immediately dissolved in about 200 ml of benzene containing p-toluenesulfonic acid monohydrate (500 mg, 2.63 mmole). The benzene solution was heated for about 2 hours under reflux with water removal facilitated by a Dean-Stark apparatus. The cooled benzene mixture was washed with aqueous $NaHCO_3$, dried (brine, $MgSO_4$) and stripped in vacuo to give crude [12a] isolated as a dark gum (4.86 g).

The above gum was dissolved in about 200 ml of dry THF and cooled to about 5° under nitrogen. Sodium hydride (876 mg, 50%, 18.25 mmole) and 2-methoxyethoxymethyl chloride (2.0 ml, 17.52 mmole) were added to the THF solution and the mixture was stirred for about 2 hours at about 5° and then for about 1 hour at about 23°. The major portion of THF was removed in vacuo. The mixture was then poured into water and extracted into ether. The organic layers were dried (brine, $MgSO_4$) and concentrated in vacuo to give 6.34 g of a light brown oil which was purified by flash chromatography (gradient 9:1 to 6:1 Hexanes:Ether) to give [13a] (2.66 g, 6.33 mmole, 42%) as a colorless oil:

IR (film) 2994, 2950, 1715, 1483, 1247, 1243, 1100, 745 cm$^{-1}$;

¹H NMR (CDCl₃)δ1.25 (s, 3H), 1.26 (t, J=7.08 Hz, 3H), 1.58–1.80 (m, 4H), 1.81 (s, 3H), 2.08 (s, 3H), 2.11 (s, 3H), 2.30 (q, J=8.0 Hz, 2H), 2.71 (m, 2H), 3.38 (s, 3H), 3.56 (m, 2H), 2.81 (m, 2H), 4.15 (q, J=7.08 Hz, 2H), 5.17 (s, 2H), 6.68 (s, 1H), 6.75 (t, J=7.35 Hz, 1H); MS m/e 420 (M+).

Anal. Calcd. for $C_{24}H_{36}O_6$:
C, 68.55; H, 8.63.
Found: C, 68.49; H, 8.63.

EXAMPLE 19

5-[3,4-dihydro-6-[(2-methoxyethoxy)methoxy]-2,7,8-trimethyl-2H-1-benzopyran-2-yl]-2-methyl-2(E)-penten-1-ol, [14a]

A suspension of aluminum hydride in ether (100 ml) was prepared from lithium aluminum hydride (1.56 g, 41 mmole) and aluminum chloride (1.819 g, 13.7 mmole). Ester [13a] (3.83 g, 9.11 mmole) was added to the alane slurry at about −5° as an ether solution (30 ml) over about 0.5 hours and stirring was continued an additional 20 minutes at about −5°. The mixture was quenched at about −5° by the careful addition of saturated sodium sulfate. The suspension was filtered and the recovered aluminum salts were triturated with hot methanol and refiltered. The organic layers were combined, washed with water, dried (brine, MgSO₄) and concentrated in vacuo to a thick oil (2.80 g) which was one spot by TLC (1:1 Hexanes:Et₂O). The recovered oil was passed through a pad of silica gel (1:1 Hexanes:Et₂O) to yield (2.80 g, 7.41 mmole, 81%) [14a] as a colorless oil to which a portion was Kugelrohr distilled for analysis (bath 200°–220°/0.1 mm):

IR (film) 3420, 2932, 1483, 1235, 1100, 1065 cm⁻¹;

¹H NMR (CDCl₃)δ1.24 (s, 3H), 1.50–1.82 (m, 4H), 1.64 (s, 3H), 2.09 (s, 3H) 2.11 (s, 3H), 2.16 (m, 2H), 2.69 (m, 2H), 3.37 (s, 3H), 3.56 (m, 2H), 3.82 (m, 2H), 3.96 (s, 2H), 5.16 (s, 2H), 5.40 (t, J=7.19 Hz, 1H), 7.68 (s, 1H); MS m/e 378 (M+).

Anal. Calcd. for $C_{22}H_{34}O_5$:
C, 69.82; H, 9.06.
Found: C, 69.45; H, 9.32.

EXAMPLE 20

3,4-dihydro-6-[(2-methoxyethoxy)methoxy]-2,7,8-trimethyl-2-(5-chloro-4-methyl-3(E)-pentene)-2H-1-benzopyran, [15a]

The procedure for the preparation of chloride [15a] from alcohol [14a] (2.71 g, 7.17 mmole) follows that described for chloride [5]. The crude chloride [15a] was purified by flash chromatography (gradient 8:1 to 4:1 Hexanes:Et₂O) to give 2.72 g, 6.86 mmole, 96% of a colorless oil:

IR (film) 2940, 1482, 1238, 1103, 1065, 685 cm⁻¹;

¹H NMR (CDCl₃)δ1.23 (s, 3H), 1.50–1.82 (m, 4H), 1.71 (s, 3H), 2.08 (s, 3H), 2.10 (s, 3H), 2.16 (m, 2H), 2.69 (m, 2H), 3.37 (s, 3H), 3.56 (m, 2H), 3.82 (m, 2H), 3.98 (s, 2H), 5.16 (s, 2H), 5.52 (t, J=7.0 Hz, 1H), 6.67 (s, 1H); MS m/e 396 (M+).

Exact mass calcd. for $C_{22}H_{33}Cl_1O_4$: 396.2067.
Found: 396.2069.

EXAMPLE 21

3,4-dihydro-6-[(2-methoxyethoxy)methoxy]-2,7,8-trimethyl-2-[(6-[(4-methylphenyl)sulfonyl]-4,8,12-trimethyltrideca-3(E),7(E),11-trienyl]-2H-1-benzopyran, [16a]

The procedure for the preparation of sulfone [16a] from chloride [15a] (2.72 g, 6.86 mmole) follows that described for sulfone [7]. The crude material was purified by flash chromatography (gradient 8:1 to 2:1 Hexanes:Et₂O) to yield sulfone [16a] (4.03 g, 6.18 mmole, 90%) as a colorless oil;

IR (film) 2980, 2930, 1600, 1480, 1455, 1145, 665 cm⁻¹;

¹H NMR (CDCl₃)δ1.17 (d, J=4.2 Hz, 3H), 1.19 (s, 3H), 1.40–1.73 (m, 4H), 1.49 (s, 3H), 1.56 (s, 3H), 1.66 (s, 3H), 1.90 (m, 4H), 2.07 (m, 2H), 2.05 (s, 3H), 2.10 (s, 3H), 2.21 (t, J=11.96 Hz, 1H), 2.41 (s, 3H), 2.66 (m, 2H), 2.83 (d, J=13.0 Hz, 1H), 3.37 (s, 3H), 3.56 (m, 2H), 3.82 (m, 2H), 3.85 (m, 1H), 4.85 (d, J=10.05 Hz, 1H), 4.99 (m, 1H), 5.13 (m, 1H), 5.15 (s, 2H), 6.66 (s, 1H), 7.27 (d, J=8.20 Hz, 2H), 7.68 (d, J=8.13 Hz, 2H); MS m/e 652 (M+).

Anal. Calcd. for $C_{39}H_{56}O_6S_1$:
C, 71.75; H, 8.65.
Found: C, 71.73; H, 8.58.

EXAMPLE 22

3.4-Dihydro-6-[(2-methoxyethoxy)methoxy]-2,7,8-trimethyl-2-(4,8,12-trimethyltrideca-3(E),7(E),11-trienyl)-2H-1-benzopyran, [17a]

The procedure for the preparation of the MEM-protected gamma-tocotrienol from sulfone [16a] (3.95 g, 6.05 mmole) follows that described for MEM-protected α-tocotrienol [8]. The crude tocotrienol was purified by flash chromatography (gradient 18:1 to 9:1 Hexanes:Et₂O) to give [17a] (2.828 g, 5.68 mmole, 94%) as a colorless oil. A portion was Kugelrohr distilled for analysis (bath 220°/0.1 mm):

IR (film) 2950, 1482, 1450, 1103, 1065 cm⁻¹;

¹H NMR (CDCl₃)δ1.24 (s, 3H), 1.50–1.82 (m, 4H), 1.58 (s, 9H), 1.66 (s, 3H), 1.90–2.10 (m, 10H), 2.09 (s, 3H), 2.11 (s, 3H), 2.69 (t, J=6.29 Hz, 2H), 3.38 (s, 3H), 3.57 (m, H), 3.82 (m, 2H), 3.82 (m, 2H), 5.08 (m, 3H), 5.17 (s, 2H), 6.68 (s, 1H); MS m/e 498 (M+).

Anal. Calcd for $C_{32}H_{50}O_4 \cdot 0.4\ H_2O$:
C, 75.97; H, 10.13.
Found: C, 75.90; H, 10.01.

EXAMPLE 23

3,4-dihydro-2,7,8-trimethyl-2-(4,8,12-trimethyltrideca-3(E),7(E),11-trienyl)-2H-1-benzopyran-6-ol [gamma-tocotrieno]

The procedure for the preparation of d,l-γ-tocotrienol from the MEM-ether [17a] (2.753 g, 5.53 mmole) follows that described for alpha-tocotrienol. The crude tocotrienol was purified by flash chromatography (gradient 18:1 to 12:1 Hexanes:Et₂O) to give a sample of gamma-tocotrienol (2.13 g, 5.2 mmole, 94%) which smelled of sulfur. The odiferous oil was rechromatographed (gradient 16:1 to 9:1 Hexanes:Et₂O) to yield gamma-tocotrienol, 1.70 g, 4.15 mmole, 75%) as an odorless, pale yellow oil which was >94% pure as determined by HPLC (IB-Sil C18 91:9 Acetonitrile:H₂O) integration:

IR (film) 3420, 2980, 2940, 2860, 1440, 1215, 1081 cm$^{-1}$;

$^1$H NMR (CDCl$_3$)δ1.24 (s, 3H), 1.50–1.82 (m, 4H), 1.58 (s, 9H), 1.66 (s, 3H), 1.90–2.10 (m, 10H), 2.10 (s, 3H), 2.11 (s, 3H), 2.66 (t, J=6.14 Hz, 2H), 4.20 (s, 1H), 5.08 (m, 3H), 6.35 (s, 1H); MS m/e 411 (MH+).

Anal. Calcd. for C$_{28}$H$_{42}$O$_2$:
C, 81.89; H, 10.31.
Found: C, 81.67; H, 10.14.

EXAMPLE 24

Ethyl 5-[3,4-dihydro-6-[(2-methoxyethoxy)methoxy]-2-methyl-2H-1-benzopyran-2-yl]-2-methyl-2(E)-pentenoate. [13b]

The sequence of steps for the preparation of ester [11b] from the allylic alcohol [10] (9.8 g, 0.046 mole) follows those described for ester [11a]. Hydroquinone-ester [11b] (7.20 g, 0.023 mole, 52%) isolated as a thick yellow oil:

IR (film) 3400, 2994, 2940, 1690, 1457, 1280, 1200 cm$^{-1}$;

$^1$H NMR (CDCl$_3$)δ1.28 (t, J=7.08 Hz, 3H), 1.63 (s, 3H), 1.84 (s, 3H), 2.28–2.39 (m, 4H), 3.28 (d, J=7.54 Hz, 2H), 4.21 (q, J=7.08 Hz, 2H), 4.46 (s, 1H), 5.34 (t, J=7.59 Hz, 1H), 6.51 (s, 1H), 6.53–6.67 (m, 2H), 6.94 (t, J=6.80 Hz, 1H); MS m/e 304 (M+).

Anal. Calcd. for C$_{18}$H$_{24}$O$_4$·0.1 H$_2$O:
C, 70.62; H, 7.97.
Found: C, 70.41; H, 7.95.

EXAMPLE 25

Benzopyranol [12b]

(1.50 g, 4.93 mmole, 94%) isolated as a pale yellow oil:

IR (film) 3420, 2980, 2950, 1715, 1690, 1500, 1290, 1220, 815 cm$^{-1}$;

$^1$H NMR (CDCl$_3$)δ1.26 (t, J=7.12 Hz, 3H) 1.26 (s, 3H), 1.60–1.90 (m, 4H), 1.80 (s, 3H), 2.28 (q, J=8.24 Hz, 2H), 2.70 (t, J=6.46 Hz, 2H), 4.15 (q, J=7.11 Hz, 2H), 4.47 (s, 1H), 6.52–6.65 (m, 3H), 6.73 (t, J=6.16 Hz, 1H); MS m/e 304 (M+).

Anal. Calcd. for C$_{18}$H$_{24}$O$_4$:
C, 71.03; H, 7.95.
Found: C, 71.03; H, 7.90.

EXAMPLE 26

MEM-ether [13b]

(1.1 g, 2.81 mmole, 61%) isolated as a colorless oil:
IR (film) 2990, 2946, 1710, 1500, 1100, 1020, 820 cm$^{-1}$;

$^1$H NMR (CDCl$_3$)δ1.26 (t, J=7.11 Hz, 3H) 1.27 (s, 3H), 1.57–1.83 (m, 4H), 1.80 (s, 3H), 2.28 (q, J=7.78 Hz, 2H), 2.72 (t, J=6.3 Hz, 2H), 3.36 (s, 3H), 3.55 (m, 2H), 3.80 (m, 2H), 4.15 (q, J=7.09 Hz, 2H), 5.16 (s, 2H), 6.62–6.81 (m, 4H); MS m/e 392 (M+).

Anal. Calcd. for C$_{22}$H$_{32}$O$_6$:
C, 67.32; H, 8.22.
Found: C, 67.15; H, 8.39.

EXAMPLE 27

5-[3,4-dihydro-6-[(2-methoxyehoxy)methoxy]-2-methyl-2H-1-benzopyran-2-yl]-2-methyl-2(E)-penten-1-ol [14b]

The procedure for the preparation of allylic alcohol [14b] from the ester [13b] (1.0 g, 2.55 mmole) follows that described for alcohol [14a]. The alcohol [14b] (0.8 g, 2.29 mmole, 90%) was recovered as a colorless oil:

IR (film) 3440, 2984, 2940, 1500, 1230, 1020 cm$^{-1}$;

$^1$H NMR (CDCl$_3$)δ1.26 (s, 4H), 1.50–1.86 (m, 4H), 1.63 (s, 3H), 2.13 (q, J=7.91 Hz, 2H), 2.71 (t, J=6.73 Hz, 2H), 3.36 (s, 3H), 3.56 (m, 2H), 3.80 (m, 2H), 3.96 (d, J=5.74 Hz, 2H), 5.15 (s, 2H), 5.38 (t, J=7.07 Hz, 1H), 6.62–6.81 (m, 3H); MS m/e 350 (M+).

Anal. Calcd. for C$_{20}$H$_{30}$O$_5$:
C, 68.55; H, 8.63.
Found: C, 68.40; H, 9.13.

EXAMPLE 28

3,4-dihydro-6-[(2-methoxyethoxy)methoxy]-2-methyl-2-(5-chloro-4-methyl-3(E)-pentene)-2H-1-benzopyran, [15b]

The procedure for the preparation of allylic chloride [15b] from the alcohol [14b] (4.20 g, 12 mmole) follows that described for allylic chloride [15a]. The allylic chloride [15b] (3.1 g, 8.41 mmole, 70%) was isolated as a colorless oil:

IR film) 2990, 2950, 1500, 1230, 1107, 1020, 685 cm$^{-1}$;

$^1$H NMR (CDCl$_3$)δ1.24 (s, 3H), 1.50–1.82 (m, 4H), 1.70 (s, 3H), 2.13 (q, J=7.22 Hz, 2H), 2.69 (t, J=6.46 Hz, 2H), 3.35 (s, 3H), 3.54 (m, 2H), 3.78 (m, 2H), 3.96 (s, 2H), 5.14 (s, 2H), 5.49 (t, J=6.08, 1H), 6.62–6.80 (m, 3H); MS m/e 368 (M+).

Anal. Calcd. for C$_{20}$H$_{29}$Cl$_1$O$_4$:
C, 65.12; H, 7.92.
Found: C, 64.79; H, 8.12.

EXAMPLE 29

3,4-dihydro-6-[(2-methoxyethoxy)methoxy]-2-methyl-2-[6-[(4-methylphenyl)-sulfonyl]-4,8,12-trimethyl-trideca3(E),7(E),11-trienyl]-2H -1-benzopyran. [16b]

The procedure for the preparation of sulfone [16b] from the chloride [15b] (3.0 g, 8.14 mmole) follows that described for sulfone [16a]. The sulfone adduct [16b] (4.50 g, 7.21 mmnole, 89%) was isolated as a colorless oil:

IR film) 2990, 2940, 1500, 1310, 1150, 820, 770 cm$^{-1}$;
$^1$H NMR (CDCL$_3$)δ1.15 (d, J<5 Hz, 3H), 1.20 (s, 3H), 1.40–1.80 (m, 4H), 1.49 (s, 3H), 1.56 (s, 3H) 1,66 (s, 3H), 1.88 (m, 4H), 2.00 (m, 2H0, 2.20 (d, J=12.15 Hz, 1H), 2m40 (s, 3H), 2.67 (m, 2H), 2.80 (d, J=13.0 Hz, 1H), 3.36 (s, 3H), 3.56 (m, 2H), 3,79 (m, 2H), 3.84 (m, 1H), 4.83 (d, J=9.87 Hz, 1H), 4.97 (m, 1H), 5.09 (m, 1H), 5.14 (s, 2H), 6.58–6.79 (m, 3H), 7.25 (d, J=8.20 Hz, 2H), 7.67 (d, J=8.15 Hz, 2H); MS m/e 624 (M+).

Anal. Calcd. for C$_{37}$H$_{52}$O$_6$S$_1$·0.2 H$_2$O
C, 70.72; H, 8.41.
Found: C, 70.47; H, 8.45.

EXAMPLE 30

3,4-dihydro-6-[(2-methoxyethoxy)methoxy]-2-methyl-2-(4,8,12-trimethyl-trideca-3(E),7(E),11-trienyl)-2H-1-benzopyran[17b]

The procedure for the preparation of MEM-ether [17b] from the sulfone [16b] (0.4 g, 6.41 mmole) follows that described for MEM-ether [17a]. The MEM-ether [17b] (2.0 g, 4.25 mmole, 66%) was isolated as a colorless oil:

IR (film) 2990, 2940, 1500, 1225, 1110, 1025, 820 cm$^{-1}$;

$^1$H MNR (CDCL$_3$)δ1.26 (s,3H), 1.50–1.84 (m, 4H), 1.59 (s, 9H), 1.66 (s, 3H), 1.90–2.14 (m, 10H), 2.71 (t,

J=6.7 Hz, 2H), 3.37 (s, 3H), 3.56 (m, 2H), 3.81 (m, 2H), 5.09 (m, 3H), 5.16 (s, 2H), 6.63–6.81 (m, 3H); MS m/e 470 (M+).

Anal. Calcd. for $C_{30}H_{46}O_4$:
C, 76.55; H, 9.85.
Found: C, 76.20; H, 9.96.

EXAMPLE 31

3,4-dihydro-2-methyl-2-(4,8,12-trimethyltrideca-3(E), 7(E),11-trienyl)-2H-1-benzopyran-6-ol [tocotrienol]

The procedure for the preparation of tocotrienol from the MEM-ether [17b] (700 mg, 1.49 mmole) follows that described for gamma-tocotrienol. Tocotrienol (400 mg, 1.05 mmole, 70%) was isolated as a colorless oil:

IR (film) 3400, 2990, 2950, 2876, 1500, 1458, 1240, 750 cm$^{-1}$;

$^1$H NMR (CDCl$_3$)δ1.26 (s, 3H), 1.50–1.84 (m, 4H), 1.58 (s, 9H), 1.66 (s, 3H), 1.90–2.15 (m, 10H), 2.69 (t, J=6.73 Hz, 2H), 4.23 (s, 1H), 5.07 (m, 3H), 6.50–6.70 (m, 3H); MS m/e 383 (MH+).

Anal. Calcd. for $C_{26}H_{38}O_2 \cdot 0.5 H_2O$
C, 79.75; H, 10.04.
Found: C, 79.67; H, 9.97.

EXAMPLE 32

3,4-Dihydro-2,7,8-Trimethyl-2-(4,8,12-Trimethyl-trideca-3(E),7(E), 11-trienyl)-2H-1-Benzopyran-6-Yl Acetate gamma-Tocotrienol (240 mg, 0.59 mmole), acetic anhydride (66 μL, 0.71 mmole), pyridine (57 μl, 0.71 mmole) and 4-dimethylaminopyridine were added to about 5 mL of dry THF and the mixture was stirred at about 23° C. for about 12 hours. The mixture was concentrated in vacuo and purified by flash chromatography (gradient 20:1 to 10:1 hexanes:ether) to yield the acetate as a colorless oil (196 mg, 0.43 mmole, 74% yield).

IR (film) 2940, 1760, 1450, 1425, 1375, 1215, 1080, cm$^{-1}$;

$^1$H NMR (CDCl$_3$)δ1.25 (s, 3H), 1.58 (s, 9H), 1.66 (s, 3H), 1.70–1.80 (m, 4H), 1.90–2.13 (m, 10H), 2.00 (s, 3H), 2.09 (s, 3H), 2.27 (s, 3H), 2.69 (m, 3H), 5.08 (m, 3H), 6.55 (s, 1H); MS m/e 453 (MH+).

Anal. Calcd. for $C_{30}H_{44}O_3$:
C, 79.60; H, 9.80.
Found: C, 79,47; H, 9.83.

EXAMPLE 33

3,4-Dihydro-2,7,8-Trimethyl-2-(4,8,12-Trimethyl 3(E), 7(E), 11-tridecatrienyl)-2H-1-Benzopyran-6-Yl-3-Pyridine Carboxylate A mixture of gamma-tocotrienol (6.47 g, 15 mmole), nicotinyl chloride hydrochoride (3.23 g, 18 mmole) and triethylamine (3.98 g, 39 mmole) were dissolved in about 200 mL of methylene chloride cooled to 5° C. After stirring for about 1 hour at about 23° C., the mixture was poured into water and the organic layers were separated and dried (brine, MgSO$_4$). The solvents were removed in vacuo and the crude material was purified by flash chromatography (gradient 9:1 to 4:1 hexanes:ether) to yield the nicotinate ester as light brown oil (7.19 g, 14 mmole, 93% yield):

IR (film) 2926 1742, 1478 1448 1422 1274 1230 1098 cm$^{-1}$;

$^1$H NMR (CDCl$_3$)δ1.28 (s, 3H), 1.58 (s, 9H), 1.66 (s, 3H), 1.70–1.85 (m, 4H, 1.90–2.13 (m, 10H), 2.05 (s, 3H), 2.13 (s, 3H) 2.73 (t, J=6.3 Hz, 2H), 5.08 (m, 3H), 6.69 (s, 1H), 7.44 (d of d, J=4.8, 7.8 Hz, 1H), 8.44 (d of t, J=1.9, 8.0 Hz, 1H), 8.83 (d, J=3.6 Hz, 1H), 9.39 (br s, 1H); MS m/e 516 MH+).

Anal. Calcd. for $C_{34}H_{45}N_1O_3$:
C, 79.18; H, 8.79; N, 2.72.
Found: C, 79.17; H, 8.81; N, 2.67.

EXAMPLE 34

3,4 Dihydro-2,7,8-trimethyl-2-(4,8,12-trimethyl 3(E), 7(E),11-tridecatrienyl)-2H-1-Benzopyran-6-Yl Butanedioate, A mixture of gamma-tocotrienol (700 mg, 1.71 mmol), succinic anhydride (190 mg, 1.88 mmole) and pyridine (203 mg, 2.6 mmole) were stirred in dry CH$_2$Cl$_2$ (10 mL) for about 15 hours at about 23° C. The mixture was poured into 1N HCl and the organic layers were separated, dried (MgSO$_4$) and concentrated in vacuo. The crude material was purified by flash chromatography (gradient 5:1 to 5:2 hexanes:ether) to yield the succinate ester as a colorless oil (500 mg, 0.98 mmole, 57% yield):

IR (film) 2650 (broad) 1760, 1725, 1440, 1380, 1150, 910, 740 cm$^{-1}$;

$^1$H NMR (CDCl$_3$)δ1.24 s, 3H), 1.58 (s, 9H), 1.66 (s, 3H), 1.70–1.80 (m, 4H), 1.90–2.13 (m, 10H), 1.99 (s, 3H), 2.08 (s, 3H), 2.68 (m, 2H), 2.78 (m, 2H), 2.86 (m, 2H), 5.08 (m, 3H), 6.54 (s, 1H); MS m/e 511 (MH+).

Anal. Calcd. for $C_{32}H_{46}O_5$:
C, 75.26; H, 9.08.
Found: C, 75.23; H, 9.13.

We claim:

1. A method of lowering the serum cholesterol levels in a bird or a mammal in need of a lowered serum cholesterol which comprises administering to such bird or mammal a safe and effective amount of substantially pure gamma-tocotrienol, substantially pure delta-tocotrienol, substantially pure tocotrienol.

2. A method of lowering the serum LDL-cholesterol levels in a bird or mammal in need of a lowered serum LDL-cholesterol which comprises administering to said bird or mammal a safe and effective amount of substantially pure gamma-tocotrienol, substantially pure delta-tocotrienol, substantially pure tocotrienol.

3. A method of lowering the serum cholesterol levels in a bird or a mammal in need of a lowered serum cholesterol which comprises administering to such bird or mammal a safe and effective amount the ester prodrug of gamma-tocotrienol, delta-tocotrienol, or tocotrienol.

4. A method of lowering the serum LDL-cholesterol levels in a bird or a mammal in need of a lowered serum LDL-cholesterol which comprises administering to said bird or mammal a safe and effective amount of the ester prodrug of gamma-tocotrienol, delta-tocotrienol, or tocotrienol.

5. The method of any one of claims 1 2, 5 or 6 wherein the tocotrienol is the d-isomer.

6. The method of any one of claims 1 2, 5 or 6 wherein the tocotrienol is the d,l racemic mixture.

* * * * *